US006585774B2

(12) United States Patent  (10) Patent No.: US 6,585,774 B2
Dean, Jr. et al.  (45) Date of Patent: Jul. 1, 2003

(54) DYNAMIC VARIABLE GEOMETRY FITTING SYSTEM FOR USE WITH A BODY APPLIANCE

(75) Inventors: Robert C. Dean, Jr., Norwich, VT (US); Michael B. Mayor, Hanover, NH (US); David F. Nelson, Norwich, VT (US); Chad S. Braley, Enfield, NH (US); Mark W. Blanchard, Orford, NH (US)

(73) Assignee: Simbex, LLC, Lebanon, NH (US)

( * ) Notice: Subject to any disclaimer, the term of this patent is extended or adjusted under 35 U.S.C. 154(b) by 0 days.

(21) Appl. No.: 09/840,955

(22) Filed: Apr. 24, 2001

(65) Prior Publication Data

US 2002/0099450 A1 Jul. 25, 2002

Related U.S. Application Data

(60) Provisional application No. 60/199,574, filed on Apr. 25, 2000.

(51) Int. Cl.⁷ .................................................. A61F 2/80
(52) U.S. Cl. ......................................................... 623/37
(58) Field of Search ............................. 623/37, 38, 36, 623/34, 33

(56) References Cited

U.S. PATENT DOCUMENTS

| 2,464,443 | A |   | 3/1949  | Ganoe et al. ......................... 3/3 |
| 3,882,561 | A |   | 5/1975  | Hanson et al. .............. 12/142 P |
| 3,942,518 | A | * | 3/1976  | Tenteris et al. ................ 128/24 |
| 4,178,013 | A |   | 12/1979 | Bataille ........................ 280/618 |
| 4,236,725 | A |   | 12/1980 | Bataille ........................ 208/611 |
| 4,662,087 | A |   | 5/1987  | Beuch ............................ 36/88 |
| 4,923,475 | A |   | 5/1990  | Gosthnian et al. ............. 623/37 |
| 5,108,456 | A |   | 4/1992  | Coonan, III ................... 623/37 |
| 5,139,523 | A |   | 8/1992  | Paton et al. ................... 623/37 |
| 5,246,464 | A |   | 9/1993  | Sabolich ........................ 623/33 |
| 5,269,811 | A |   | 12/1993 | Hayes et al. .................... 623/3 |
| 5,353,525 | A |   | 10/1994 | Grim .............................. 36/88 |
| 5,376,127 | A |   | 12/1994 | Swanson ...................... 623/27 |
| 5,464,443 | A |   | 11/1995 | Wilson et al. ................. 623/37 |
| 5,466,250 | A | * | 11/1995 | Johnson, Jr. et al. ....... 607/104 |
| 5,588,955 | A | * | 12/1996 | Johnson, Jr. et al. ....... 601/152 |
| 5,658,353 | A |   | 8/1997  | Layton ......................... 623/34 |
| 5,735,906 | A | * | 4/1998  | Caspers ....................... 623/34 |
| 5,813,142 | A |   | 9/1998  | Demon .......................... 36/29 |
| 5,904,721 | A |   | 5/1999  | Henry et al. .................. 623/26 |
| 6,231,616 | B1 |  | 5/2001  | Helmy .......................... 623/34 |

FOREIGN PATENT DOCUMENTS

WO   PCT/US02/08898   3/2002

OTHER PUBLICATIONS

Porten, L.; *Self–Adjustable and Inflatable Air Stump Socket*; Orth. Pros. Appl. J.; 382–385; Dec. 1963.

(List continued on next page.)

*Primary Examiner*—Corrine McDermott
*Assistant Examiner*—Alvin Stewart
(74) *Attorney, Agent, or Firm*—Perkins, Smith & Cohen, LLP; Peter J. Borghetti; Jacob N. Erlich

(57) ABSTRACT

A dynamic variable geometry fitting system with fluid-filled bladders and automatically regulating their volumes to provide a continuously secure fit. This system can vary volume continuously to accommodate natural variation in an amputee's residuum. It makes reliable suction retention of a prosthesis easier for the prosthetist to achieve while reducing the potential for tissue lesions. By maintaining a continuous, secure fit, the amputee's sense of confidence and willingness to use the prosthesis increases.

49 Claims, 9 Drawing Sheets

OTHER PUBLICATIONS

Porten, L; *Addendum: Self Adjustable and Inflatable Air Stump Sockets*; Orth. Pros. Appl. J.; 138–140; Jun. 1964.

Volkert, R.; *Frame Type Socket for Lower Limb Prostheses*; Pros. Orth. Int'l.; 6:88–92; 1982.

Kirstinsson, O.; *Flexible Above–Knee Socket Made from Low Density Polyethylene Suspended by a Weight Transmitting Frame*; Orth. Pros.; 37(2):25–27; 1983.

Sabolich J,; *Contoured Adducted Trochanteric–Controlled Alignment Method (CAT–CAM): Introduction and Basic Principles*; Clin. Pros. Orth.; 9(4):15–26; 1985.

Jendrzejczyk, D. J.; *Flexible Socket Systems*; Clin. Pros. Orth.; 9(4):27–31; 1985.

Long, I. A.; Normal Shape–Normal Alignment (NSNA) Above–Knee Prosthesis; Clin. Pros. Orth.; 9:9–14; 1985.

Roberts, R. A.; *Suction Socket Suspension for Below–Knee Amputees*; Arch. Phys. Med. Rehabil. 67(3):196–199; 1986.

Staats, T. B. et al; *The UCLA Total Surface Bearing suction Below–Knee Prosthesis*; Clinical Pros. And Orth.; 11(3):118–1301; 1987.

Schuch, M.; *Modern Above–Knee Fitting Practice*; A report on the ISPO Workshop on Above–Knee Fitting and Alignment Techniques; May 15–19, 1987, Miami, FL; Pros. Orth. Int'l.; 12:77; 1988.

Michael, J. W.; *Current Concepts in Above–Knee Socket Design*; Amer. Acad. of Orth. Surg.; Instr. Course Lecture; 39:373–378; 1990.

Michael, J. W. et al; *New Developments in Recreational Prostheses and Adaptive Devices for the Amputee*; Clin. Orth. and Rel. Res.; 256:64–75; Jul. 1990.

Houston, V. L. et al, Automated *Fabrication of Mobility Aids (AFMA): Below–Knee CASD/CAM Testing and Evaluation Program Results*; J. Rehab. Res. Dev.; 29(4):78–124; 1992.

Sabolich, J. et al; *Below–Knee Prosthesis with Total Flexible Socket*; Preliminary Report Clin. Pros. Orth.; pp. 93–99; Spring 1996.

Hachisuka, K. et al; *Total Surface Bearing Below–Knee Prosthesis: Advantages, Disadvantages, and Clinical Implications*; Arch. Phys. Med. Rehab.; 79(7):783–789; 1998.

Haberman, L. J.; *A New and Improved Pre–Fabricated Silicone Liner for the Transtibial Amputee*; Proceedings 1996 AOPA National Assembly; Oct. 1996. (not available at this time).

* cited by examiner

A = Anterior   D = Distal   L = Lateral   M = Medial   P = Posterior   x = Proximal A = Anterior  D = Distal  L = Lateral  M = Medial  P = Posterior  x = Proximal

DYNAMIC VARIABLE GEOMETRY FITTING SYSTEM FOR USE WITH A BODY APPLIANCE

CROSS REFERENCE TO RELATED APPLICATIONS

This application claims priority of Provisional Application No. 60/199,574, entitled Lower-Limb Prosthesis Socket System and Its Production and Use filed on Apr. 25, 2000, and which is incorporated herein by reference.

STATEMENT OF GOVERNMENT INTEREST

This invention was made with U.S. Government support from the National Science Foundation, No. DMI-9960955, and National Institutes of Health Small Business Innovation Research, Nos. R43 HD36154-01, -02. The U.S. Government has certain rights in the invention.

BACKGROUND OF THE INVENTION

This invention relates generally to a dynamic variable geometry fitting system for continuously maintaining a secure fit of an external appliance to a body segment, and, more particularly to, a variable geometry system for use with a lower-limb-prostheses.

Lower-limb amputees typically have difficulty maintaining a comfortable, yet secure attachment of their prosthesis to their residual limb (residuum). The volume of the residuum fluctuates both throughout the day and periodically as a result of normal physiological mechanisms. The amputee can detect very small changes in residuum volume. These volume variations often will decrease stability and cause maldistribution of weight-bearing forces, increase locomotion effort, exacerbate insecurity and even cause detachment of a suction-retention socket.

The socket is the mechanical connection between a lower-limb prosthesis and the amputee's anatomy. As such, the quality of socket fit is usually the most critical determinant of the amputee's satisfaction with his prosthesis. The precise fitting of the socket and the maintenance of a precise fit are extremely important to the amputee's comfort, skin integrity, sense of ambulatory security and stability, and locomotion effort.

When an adequate socket fit is finally obtained by the prosthetist, frequently after much trial and error fitting often requiring several check sockets, this fit cannot easily be maintained. Modern fabrication techniques using advanced tools such as CAD/CAM may reduce the iterations required to achieve an initial socket fit. Even using these techniques, initial precise socket fit is frequently lost due to natural volumetric changes of the residuum. Unfortunately, such volumetric change of the residuum is unavoidable. Such change can occur hourly, daily and monthly. For many amputees, the residuum is in a constant state of volumetric flux.

Modern Medial-Lateral (ML) transfemoral (TF) sockets are very sensitive to residuum volume variations which can cause, late in the day, intolerable pain in the groin. This is because the M-L socket is designed to carry about 40% of the load with soft-tissue hydraulic pressure and about 60% by ischial tuberosity support. When the tissue shrinks, the hydraulic support diminishes rapidly. The volume shrinkage then drops the TF residuum into the socket causing its medial brim to load excessively the tissue over the ischial ramus and adductor longus.

A volume change of just 0.2% in a 1500 ml transfemoral total-contact socket can alter the amputee's perception of ambulatory security. Further, a volume change of 1% was sensed as a "sloppy fit" by wearers of transfemoral (TF) total-contact, suction-retention sockets. A volume change of 5–6% can cause detachment of a suction-retention socket.

Transtibial (TT) amputees typically have a diurnal variation in residuum volume that requires the addition of one to several single-ply stump socks, from morning to evening, in order to maintain a tight fit. For the typical TT residuum (girth=100 mm; L=150 mm) and stump sock thickness (t=2 mm), two of these sock additions can amount to a volume change of about 2.7%. A residuum volume change of such magnitude, without compensation, is intolerable. For this reason, some TT amputees must continue to don greater numbers of socks during the day in order to maintain a satisfactory fit. Large and frequent volumetric changes of the TT residuum make it difficult to achieve and maintain proper socket contact pressures and compression. Consequently, TT amputees are often unable to utilize effectively and benefit from the suction-retention socket, which requires a tight, non-leaking fit in order to maintain the suction needed to retain the TT prosthesis. This consequence is very unfortunate because a poorly fitting suction socket is usually intolerable, so such afflicted TT amputees may be forced to abandon use of their prostheses. The efficacy of both TF and TT lower-limb prostheses is often reduced due to uncompensated soft-tissue volume variations, which are unavoidable and occur regularly.

Further, suction pressure during the swing phase and positive pressure during the stance phase, of the walking cycle, with a suction socket, has been shown to be beneficial to the TT amputee's residuum skin and tissue health. Severe lesions, cysts and abrasion have actually been cured by use of a suction socket by TT amputees. This is especially true with a dysfunctional vascular system in the residuum, and such vascular dysfunction is the leading cause of TT amputations.

A further difficulty with all of these present day socket-fitting means is that when the residuum swells, the intra-socket pressure will become intolerable when the residuum swells, and could even result in ischemia (i.e., pinching of the capillaries stops blood flow to tissue), if the socks are not removed in a timely fashion.

Today, prosthetists most often manage residuum volume shrinkage by adding socks, making new sockets or by internal padding of existing sockets. These approaches are entirely inadequate to accommodate natural diurnal volume changes and the weekly and monthly volume variations of the ill, the diabetic, the kidney dialysis patient and the menstruating woman. Furthermore, the accommodation of residuum atrophy of new amputees, accomplished by manufacturing multiple sockets, is very expensive, even using modern CAD/CAM fabrication.

Many different types of variable-volume sockets have been proposed and tried, but none of these apparatuses address adequately the fundamental problem of automatically adjusting for volumetric change of the residuum.

It is the object of this invention to provide a dynamic variable geometry fitting system for use in, for example, lower-limb prostheses that continuously maintains a secure fit of an external appliance to a body segment.

It is a further object of this invention to provide a variable geometry system for use in lower limb prostheses, which automatically accommodates to the amputee's normal variation in residuum volume while maintaining a secure fit.

It is still a further object of this invention to provide a low-compliance attachment between the amputee's residuum and the prosthesis and which reduces the portent of tissue damage and/or discomfort as well as reducing incidences of instability and insecurity due to poor fit.

It is even another object of this invention to provide a system that improves for the prosthetist the reliability of fitting suction-type sockets and reduces the extent of trial-and-error fitting.

It is still another object of this invention to provide a continuously adjustable prosthesis attachment to the anatomy, which accommodates natural, physiological volume changes of the amputee's residuum.

It is yet another object of this invention to provide a means for employing and automatically regulating fluid fill in bladders within a prosthesis socket.

It is a further object of this invention to resolve stump-volume sensitivity.

It is still a further object of this invention to provide a means for increasing appliance volume for easy donning and doffing of the appliance.

It is another object of this invention to provide a dynamic variable geometry fitting system for maintaining secure fit of external appliances, such as shoes, boots, braces, wraps, garments to various body segments of humans and other animals.

It is a further object of this invention to provide a device for improving comfort of an external appliance applied to the body of humans and other animals by allowing dynamically adjustable pressure regulation.

SUMMARY OF THE INVENTION

The objects set forth above as well as further and other objects and advantages of the present invention are achieved by the embodiments of the invention described hereinbelow. Briefly stated, the present invention provides a means for achieving dynamically variable geometry adjustable fit of an external appliance to a body segment of a human or other animal. For example, one embodiment of the present invention gives prosthetists a dynamic fitting system the use of which will provide lower-limb amputees with prostheses that maintain automatically a secure and comfortable fit throughout normal residuum volume fluctuation. The system employs the advantages of using incompressible fluid fill in the bladders rather than compressible gas fill. One or more of the bladders serves as a pump, energized by walking, for example, which is regulated by a control system. Once donned, the entire system requires neither manual intervention nor an outside power source to function. This embodiment of the present invention adjusts the socket volume automatically in order to maintain a proper fit on a transfemoral (TF) or transtibial (TT) residuum or other body-fitting appliances. However, the dynamic variable geometry fitting system is adaptable to other body appliances such as ski boot, boots (including sports boots), shoes, sneakers, prosthetic appliance, orthopedic appliance, brace, or body part wrap, and virtually anything that is designed to be worn on a body part.

For a better understanding of the present invention, together with other and further objects thereof, reference is made to the accompanying drawings and detailed description and its scope will be pointed out in the appended claims.

DETAILED DESCRIPTION OF THE PREFERRED EMBODIMENTS

The preferred attachment system includes a set of variable-volume bladders that are adjusted in volume by a fluid-pumping mechanism actuated through ambulation without an external energy source and are automatically regulated. The system utilizes a bladder to pump fluid automatically from a reservoir through a fluid circuit to bladders and a control unit.

Figure 1:
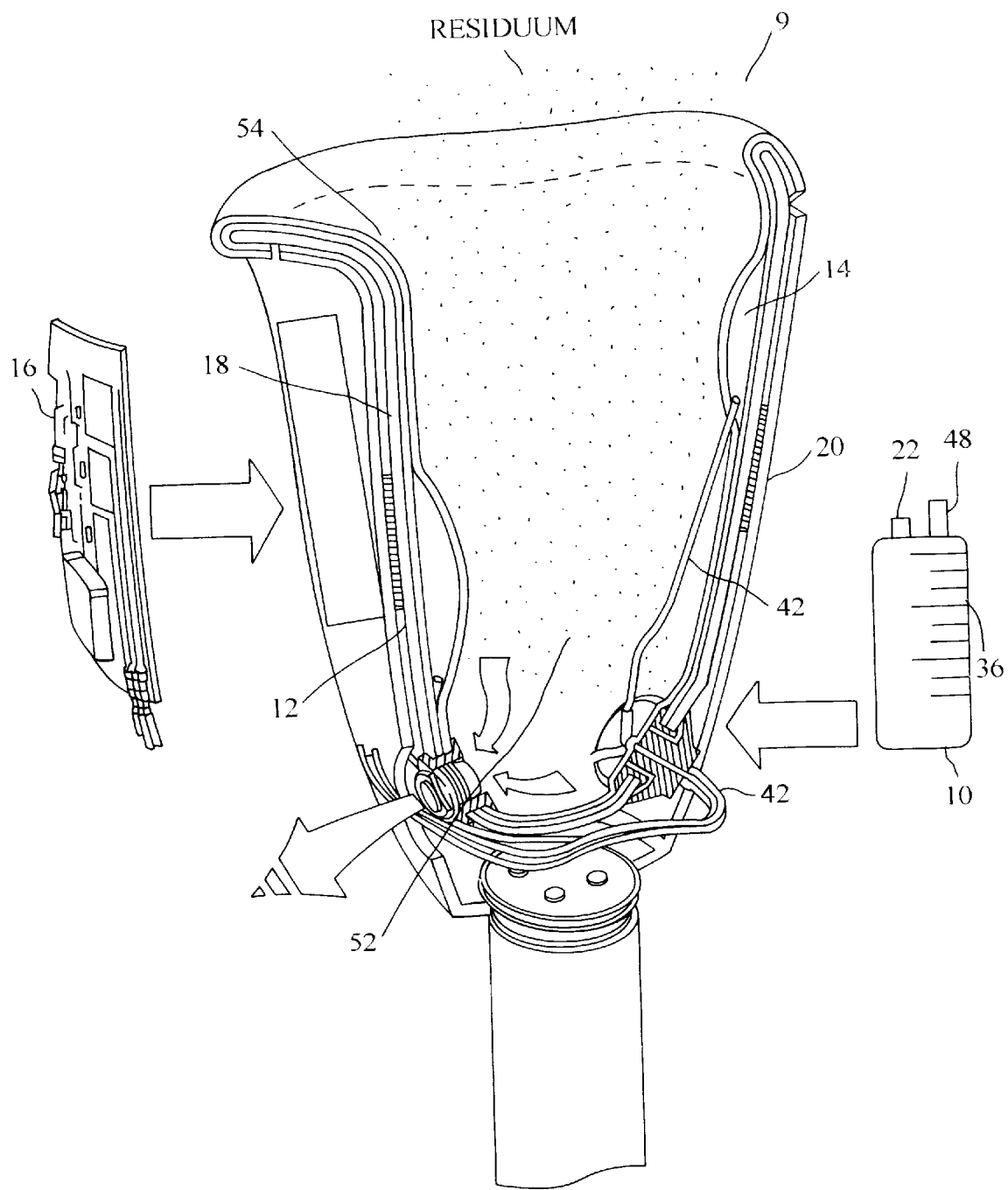
FIG. 1 is a pictorial view of the dynamic variable geometry fitting system of the invention adapted to use with a prosthesis.
Figure 3A:
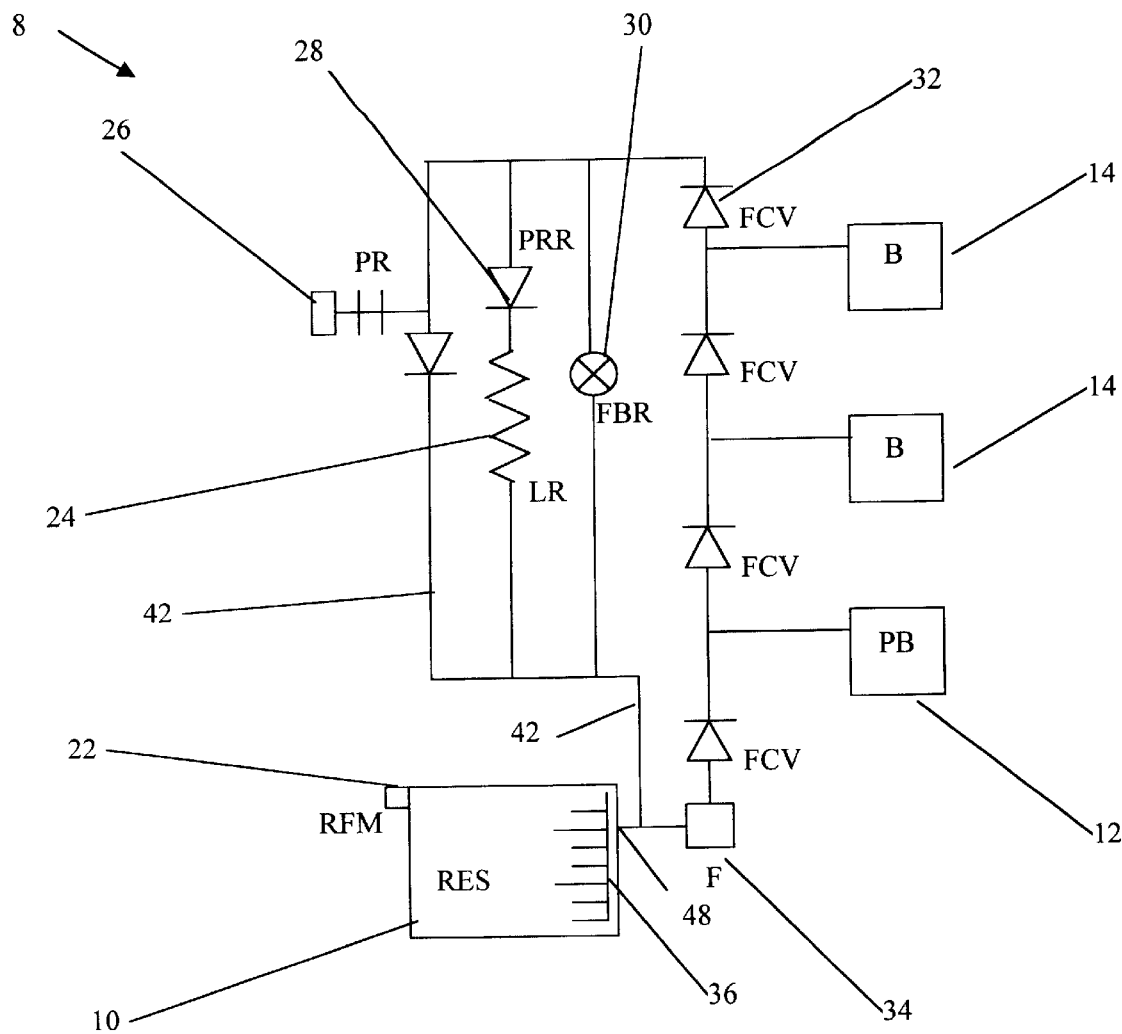
FIG. 3a is a schematic representation of the preferred embodiment control system of this invention for a single set pressure.

The preferred attachment fitting system 8 of this invention, FIGS. 1 and 3a, which is utilized to removable adhere a body appliance 9, such as a prosthesis, to a body part or appendage, includes a reservoir 10, one or more variable-geometry pumping bladders 12, a plurality of variable-geometry pressure bladders 14, an interconnecting network, and a control unit 16. The aforementioned components work in cooperation to maintain a tight fit of the body appliance on, for example, a residuum (shown in phantom), or other body segment. The residuum is placed within a cavity, such as the socket cavity 54 with the body appliance 9, while ambulating to relieve potential ischemia during stasis and to permit easy donning and doffing of a prosthesis 9. The preferred attachment fitting system can be placed within and around a flexible or rigid vessel, such as the socket 18 and frame 20 of a lower-limb prosthesis (shown in phantom).

The preferred fluid to use in the attachment fitting system 8 is an incompressible liquid such as water with antifreeze, such as calcium chloride added in cold weather to prevent freezing when the prosthesis is doffed. However, other low-viscosity, incompressible fluids such as isopropyl alcohol, light silicon oil or any other biocompatible, safe fluid may be employed. Alternative fluid embodiments include gels, multiphase fluids, or any other fluids with substantially incompressible properties are within the scope of this invention.

For background information, about 80% of the volume of, for example, a TF residuum is soft tissue. When this tissue shrinks, by loss of liquid, the intra-socket void between the soft tissue of the limb and the shell of the socket must be filled with something else. For a standard fixed-volume socket, that "something else" will be air, which is immediately detectable by the amputee and significantly affects the fit and performance of the prosthesis. When the residual soft tissue shrinks in volume, it loses liquid to the lymph and vascular systems. The soft tissue contains no gas pockets; it is comprised of about 80% liquid, so it behaves physically like a liquid. Therefore, in order to approximate physiological conditions in the socket, the shrinkage void is back-filled with liquid in the present invention. Then the compliance, or compressibility, of the matter filling the socket will remain constant.

In contrast, if the shrinkage void is filled with gas, the filling is 20,000 times more compressible (at 1 bar, 30° C.) than a liquid-fill. So the gas-filled bladder will expand and contract in volume in a fashion drastically different from soft tissue of the residuum. The pressure-displacement (P-D) compliance will be large, engendering excessive "pumping," loose coupling of the socket to the anatomy and a feeling of insecurity. Insecurity is due to sloppiness of the joint between the anatomy and the mechanism, causing uncertainty as to where is the ambulating foot, and in addition, for the TF amputee, whether the knee joint is safely locked for weight-bearing during the stance phase of the walking cycle.

Figure 2A:
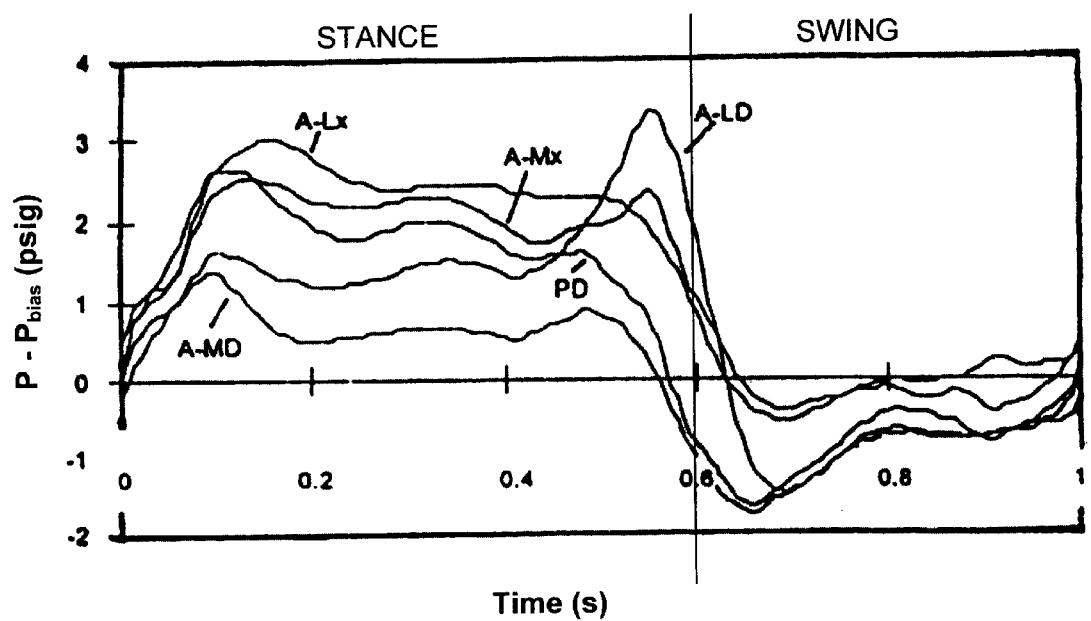
FIG. 2a shows an intra-socket pressure trace of a transfemoral amputee walking on a hard floor.
Figure 2B:
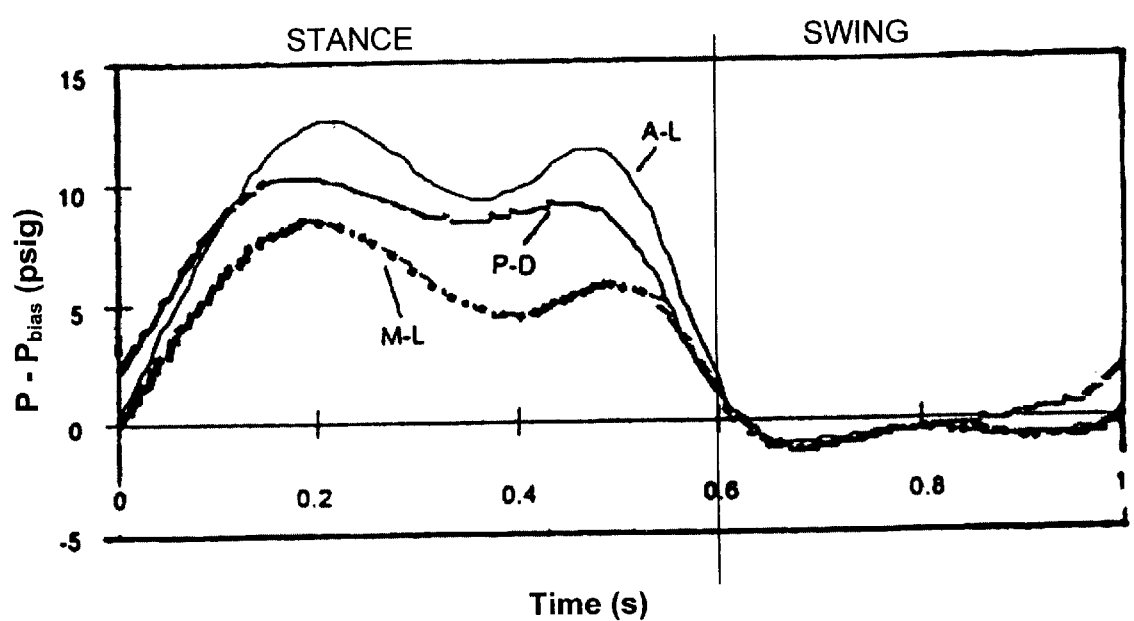
FIG. 2b shows an intra-socket pressure trace of a transtibial amputee walking on a hard floor.

Using the laws of gas and liquid responses to a pressure change, the P-D compliance may be calculated from intra-socket pressure data. A sample of intra-socket pressure data is illustrated in FIGS. 2a and 2b in which are plotted intra-socket pressures vs. time. FIG. 2a is from a TF amputee; FIG. 2b is from a TT amputee. The cycle time has been normalized for both. Pressure sensors were positioned in various intra-socket locations within the sockets of TF and TT amputees. The subjects then walked on a hard floor while pressure data were recorded. Data were averaged from many stride cycles to create the graphs in FIGS. 4a and 4b. The pressure data were then transformed, by the perfect-gas and the liquid laws, into hypothetical bladder volume variations for a stride cycle when bladder filled volume equals a typical 10% of socket volume, FIGS. 4a and 4b. Results are shown for air-filled and liquid-filled bladders, for TF (FIG. 4a) and TT (FIG. 4b). The plots have been averaged and time normalized as before. Note the great difference in compliance (compressibility) between air-filled bladders and liquid-filled bladders during a typical stride cycle.

Figure 4A:
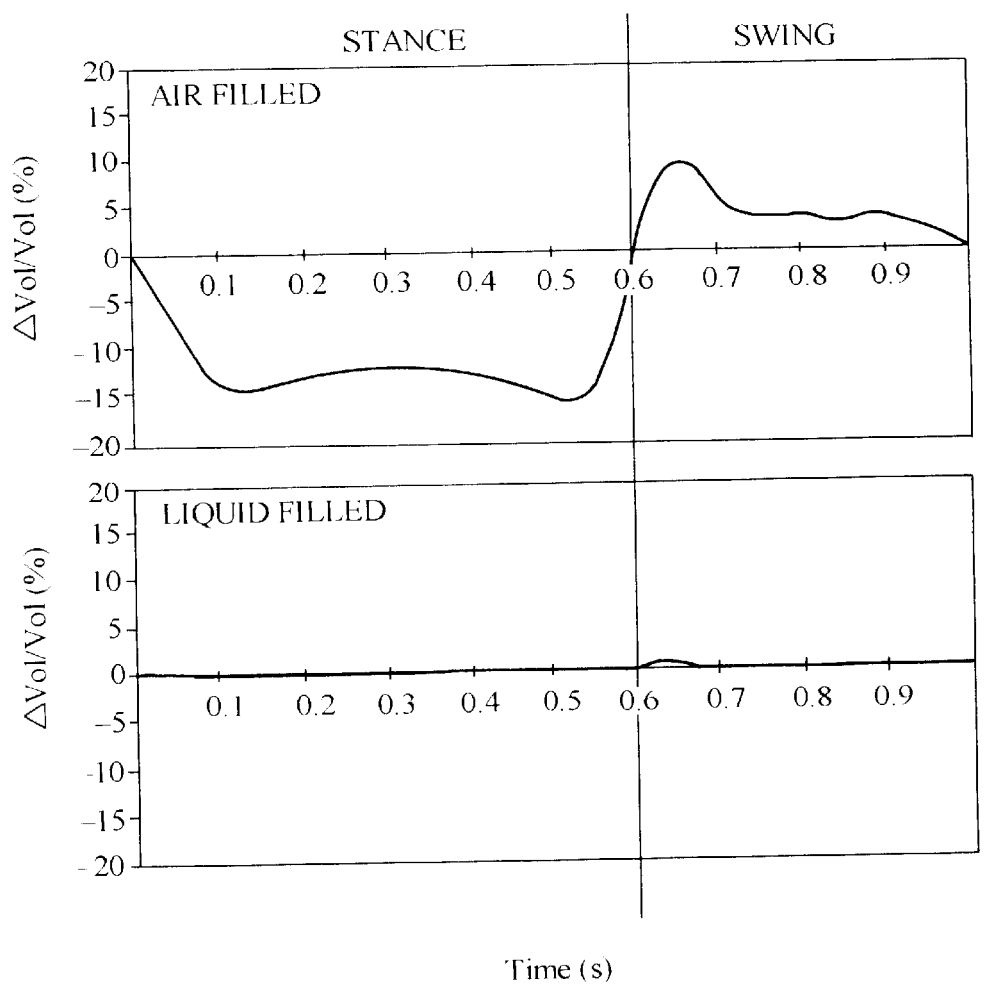
FIG. 4a shows pressure-displacement traces of an intra-socket bladder filled with air and liquid of a transfemoral amputee walking on a hard floor.
Figure 4B:
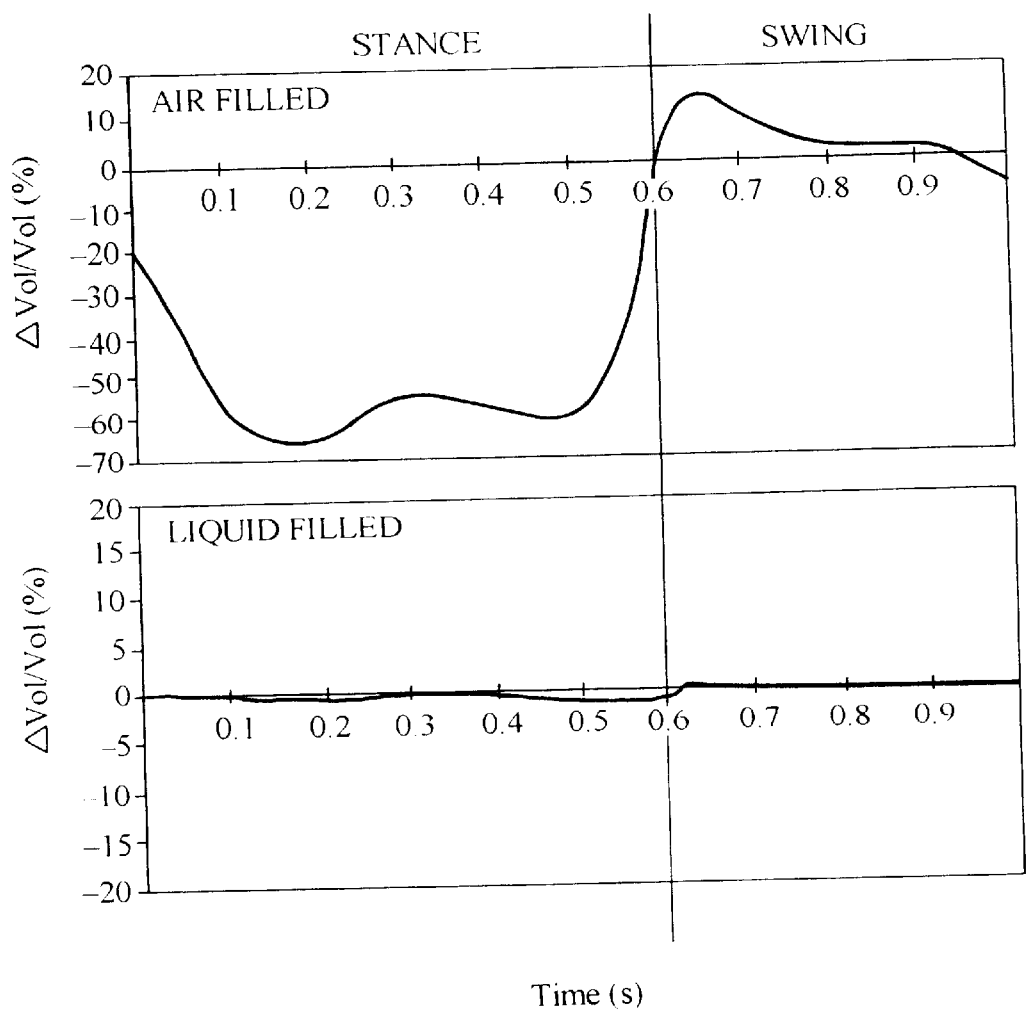
FIG. 4b shows pressure-displacement traces of an intra-socket bladder filled with air and liquid of a transtibial amputee walking on a hard floor.

The P-D compliance may be calculated by dividing $\Delta$Vol, FIGS. 4a and 4b, by the mean cross-sectional area of the socket (typically 0.018 m$^2$ for TF and 0.008 m$^2$ for TT) times the length. For example, the peak TT $\Delta$Vol/Vol in FIG. 4b is about 60% for air-filled and 1% for liquid-filled bladders. These $\Delta$Vols convert, for this TT socket (1000 ml), to P-D "pumping" strokes of 8 mm for air fill and 0.1 mm for liquid fill, respectively. With an 8 mm P-D stroke (and no mechanical retention), the TT socket of a suction-retention-only prosthesis fitted with an air-filled bladder probably would detach from the residuum. In contrast, the prosthesis fitted with a liquid-filled bladder as in the present invention would remain firmly attached.

Raising the pressure in gas-filled bladders is thought by some to be the solution to reducing their compliance (compressibility). However, the compressibility of gas (dp/dVol) varies as $p^{k+1/k}$ where k=ratio of specific heats. So, inflating the bladders to 3 bar (28.8 psig) would increase stiffness by only 3.25 times. Then the maximum bladder volume change (FIG. 4b) for air-filled TT bladders would decrease to 20%, which is still intolerable. Furthermore, this tactic is impossible because such pressure (which would need to be applied continually) would greatly exceed the ischemic limit (~25 mm Hg above ambient), leading to tissue necrosis.

Figure 3B:
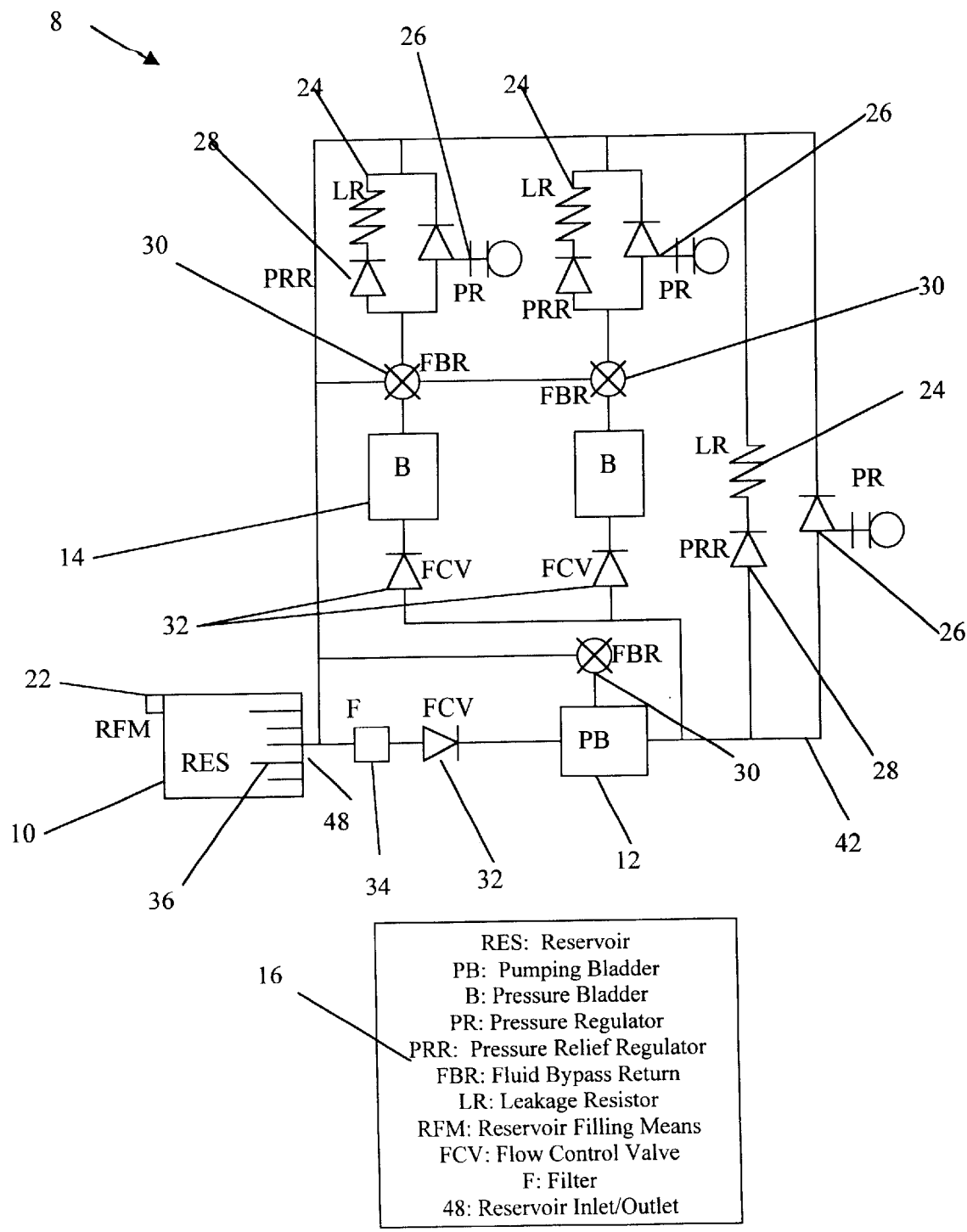
FIG. 3b is a schematic representation of the preferred embodiment control system of this invention for a multiple set pressure.

Referring now to FIGS. 1, 3a, and 3b, the reservoir 10 is a fluid-container that is made of a flexible or rigid non-leaking material, such as a silicon or urethane, to maintain a reservoir internal pressure. The reservoir capacity for normal TF and TT are 200–300 ml and 100–250 ml, respectively. The reservoir 10 can be sealed or open to ambient depending on the predetermined reservoir pressure. The internal reservoir pressure is set for the particular application, suction or non-suction socket. For a suction socket in a lower-limb prosthesis, the reservoir pressure can be set at ambient pressure. For a non-suction socket, the reservoir pressure can be set to be above or below ambient pressure. The reservoir interior pressure can be set be various means, including conventional springs or bellows (not shown).

In the preferred attachment system, the reservoir 10 also includes a reservoir filling means 22 to allow fluid to be added to or removed from the reservoir 10. The reservoir filling means 22 is a septum (not shown). The septum is penetrated by a needle or other means to add or remove fluid.

The reservoir 10 further includes an inlet/outlet 48 to feed fluid to the system during the pressurization cycle and to receive excess fluid from the system when the system pressure exceeds set pressure limits or when the pressure bladders 14 and pumping blade 12 are drained for body appliance removal.

Additionally, an alternative embodiment of the reservoir may be fitted with a volume scale 36, FIG. 1, to indicate the need for refill and in testing to serve as an indicator of fluid-consumption.

In the preferred attachment fitting system 8, the pumping bladder 12 is positioned such that it will experience a pressure below reservoir pressure (negative pressure), thereby drawing fluid from the reservoir 10, and a pressure above reservoir pressure (positive pressure), thereby pumping to pressure bladders 14, during some phase of the pumping cycle. An example of a pumping cycle is a walking cycle characterized by a stance phase (positive pressure) and a swing phase (negative pressure). There must be a sufficient difference in pressure created between the reservoir 10 and the pumping bladder such that fluid flows into the pumping bladder 12. The pumping bladder 12 is positioned near the distal-end 52 of the socket 18 so that it will experience, in a suction socket during the swing phase of normal ambulation, a pressure below the reservoir pressure. However, the pumping bladder can be positioned anywhere within the socket 18 providing the pressure characteristics are maintained.

A plurality of pressure bladders 14, see FIGS. 1, 3a, and 3b, are placed such that fluid pumped from the pumping bladder 12 is channeled to discrete locations for volume management and controlled pressure. For TF sockets, the fully inflated volume of each pressure bladder 14 is approximately 100 ml. One or more pressure bladders 14 can be placed in the superficial groove between the vastus lateralis and biceps femoris (longhead) muscles to prevent rotation of the socket 18 on the residuum, as well as to secure the socket 18 to the residuum. For TT sockets, the pressure bladders 14 are usually smaller, approximately 30–40 ml volume fully inflated. One or more pressure bladders 12 are placed on the medial and lateral tibial aspects and above and below the femoral condyles. The size and shape of these pressure bladders 14 can be variable and determined by the prosthetist.

As illustrated in FIGS. 1 and 3a, the preferred embodiment control system 16 for attachment fitting system 8 includes a filter 34, a plurality of pressure regulator(s) 26, pressure relief regulator(s) 28, leakage resistor(s) 24, fluid bypass return 30, connected by conduit(s) 42 and flow control valve(s) 32 to form a fluid circuit. The control system 16 illustrated in FIG. 3a regulates pressure in all of the bladders by a single pressure regular 26.

Figure 5A:
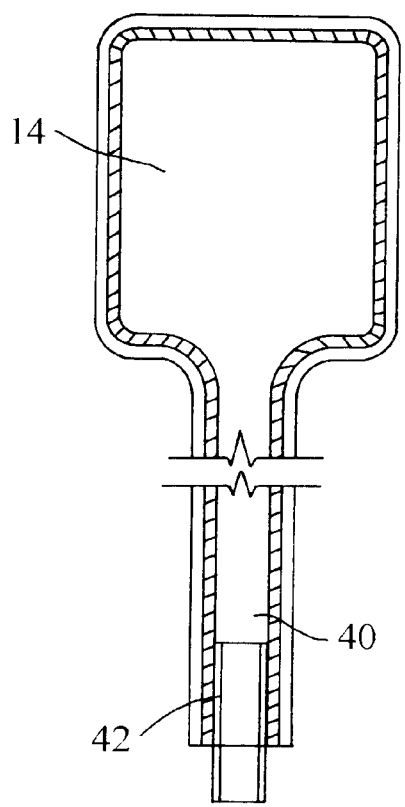
FIG. 5a shows a top view of a bladder of this invention.

In the preferred attachment fitting system 8, the pumping bladder 12 and pressure bladders 14 are constructed of a biocompatible medical grade urethane material that has a relatively low perfusion rate, approximately 1% of the bladder volume per day, to prevent the need for frequent refilling of the reservoir 10. Higher perfusion rates are acceptable, but the amputee may be inconvenienced with more frequent fillings of the reservoir 10. As shown in FIG. 5a, All bladders include a bladder inlet 40 to receive the conduit 42. An alternative material includes non-biocompatible urethane where the residuum is not in direct contact with bladder.

For example, a 25 um (micron) commercially available filter 34 is placed in-line between the reservoir 10 and the pumping bladder 12 to prevent particulate debris from entering the bladders and potentially clogging the conduits 42, pressure regulators 26, pressure relief regulators 28, and leakage resistors 24.

The pressure regulator(s) 26 are situated between the bladder(s) 12 and 14, and the reservoir 10 to allow for excess fluid to return to the reservoir when the pressure exceeds a predetermined pressure. The pressure regulator(s) 26 are set to the highest comfortable level for the user, which allows the tightest comfortable fit. For lower-limb prostheses, the set pressure can be permanent or adjustable. TF amputees typically feel comfortable with equal pressure in 2–5 bladders within socket 18. FIG. 3a shows a single, pressure regulator 26, which sets the same pressure in all of the bladders because they are interconnected as shown. The control system 16 can use adjustable pressure regulators or ones with fixed set points. With the latter method, the pressure is adjusted in the bladders by exchanging pressure regulators with different set points until the user is satisfied. When amputees first start wearing the system, they usually prefer a lower pressure level than they do after several weeks of use. Adjustable pressure regulators allow for continuous modification of the set pressure level. Once a preferred pressure level has been established for each amputee, that pressure setting usually remains constant.

The pressure relief regulator 28 and a leakage resistor 24 are placed in parallel with the pressure regulator 26. The pressure relief regulator 28 is set to a value lower than the pressure regulator 26. A leakage resistor 24 is designed to drop the pressure in the pressure bladders 14 to the set pressure of the pressure relief regulator 28. For lower-limb prostheses, the pressure relief regulator 28 is set to approximately 0.5 psig. The leakage resistor 24 helps to prevent tissue ischemia. When ambulation is stopped, the leakage resistor 24 allows the pressure to drop below the ischemic limit (~25 mm Hg above ambient) in a time span of a few minutes as fluid flows back to the reservoir 10 through the leakage resistor 24. The pressure relief regulator 28 can be adjustable or with fixed set points.

A fluid bypass return 30 allows rapid return of all fluid to the reservoir, emptying all bladders. The fluid bypass return 30 is a manually actuated preferably mechanical switch. Commercially available alternative methods of the fluid bypass return 30 include other mechanical or electromechanical switches or valves, thermally controlled switches, or magnetically controlled switches.

Figure 5B:
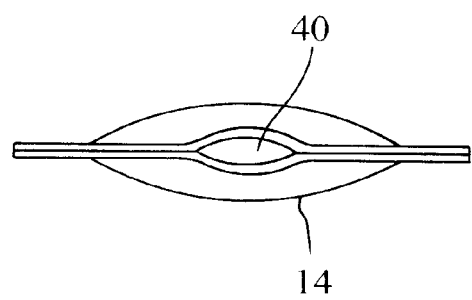
FIG. 5b shows a front view of a bladder of this invention.

Small conduits 42 connect the various system components allowing a closed loop fluid circuit. The conduit 42 is made of a pliable, durable material with an inner diameter (e.g., 1–2 mm bore) sized for a quick and smooth response to the pumping action and an outer diameter that is sized to fit snuggly within the bladder inlet 40 to avoid leaks, see FIG. 5a and FIG. 5b.

Flow control valves 32, such as check valves, prevent fluid from flowing among the pressure bladders 14 and back into the pumping bladder 12, and from the pumping bladder 12 back into the reservoir 10.

The pressure regulator 26, pressure relief regulator 28, and flow control valves 32 are commercially available mechanical valves which may be spring loaded, diaphragm style, or "duckbill" elastomer. Alternatives to physical valves include tuned valves, such as acoustic valves, thermally regulated valves or electrically operated valves, or magnetorheologic fluids well known in the art used in conjunction with magnetic fields, could perform the same function as the spring loaded mechanical valves.

An alternative embodiment to the control system 16 is illustrated in FIG. 3b. The alternative control system regulates pressure for each of the bladders 14 separately. Each of the bladders 14 are set at different levels by individual pressure regulators 26, pressure relief regulators 28, and flow bypass returns 30. The system components are the same as the attachment system disclosed in FIG. 3a.

The control principle of this invention for example, in use with a lower limb prosthesis is to maintain set pressures in the pressure bladders 14, which bear against a liner, such as Alpha® or a thin elastomer sheet, and then onto the residuum. Alternatively, the bladder 14 may bear directly against the residuum. The bladders 14, fluid-filled completely, fill voids in the socket 18 and exert forces against the socket frame 20 and the residuum, which maintains the socket at a preset tightness. Generally, the tighter the socket, the lower the compliance between the prostheses and the anatomy. The residuum "pumping" (relative superior-inferior motion between socket and residuum), which can cause skin abrasion and lesions, is reduced the more natural the prosthesis feels and the more securely and competently the amputee can manipulate it. In order to achieve minimum compliance, the pressure in the bladders 14 is set to the highest comfortable level.

Another feature of the control system 16 is that the pressures applied to the tissue must be relaxed during stasis (i.e., when not walking). Without the pressure fluctuations of ambulation, there is a threat of tissue ischemia (constricted capillaries stop blood flow) and consequent tissue necrosis. If a pressure higher than ~25 mm Hg above ambient is applied to the skin for extended time periods, such as more than about 30 minutes, the compressed tissue is starved of blood flow from its capillaries. The control system 16 automatically relaxes the pressure against the tissue by a slow leak through leakage resistor(s) 24, to below the ischemic limit if stasis is maintained for more than a few minutes. The pressure relief regulator 28 sets the resulting pressure in the bladder(s) 14. The leakage resistor 24 provides a means for returning fluid to the reservoir 10 slowly without completely emptying the bladders 14. In the absence of the leakage resistor 24, the pressure in the pressure bladders 14 would remain at the set pressure until the fluid bypass return was activated or until fluid perfused through the pressure bladder wall.

A further aspect of the control system 16 is that, when an amputee commences to walk again after stasis, the socket should be tight, despite the fact that the bladder pressures have been relaxed. Proper pressure magnitude and distribution in the socket are automatically maintained, for TF and TT sockets, for a tight fit during ambulation. During long-term sitting, it automatically lowers the pressure in bladder(s) 14 to less than the ischemic limit (~25 mm Hg above ambient). Because of the incompressibility of the bladder fluid and of the tissue, and the rigidity of the socket 18, this pressure relief is achieved by extracting a very small volume of fluid, approximately 0.5 ml, from each bladder through leakage resistor(s) 24 and pressure relief regulator (s) 28. This means that the inside geometry of the socket should change little when the pressure in the bladders is relaxed, so that the prosthesis is not significantly loose on the residuum. Within approximately 10–20 steps after walking recommences, the control system 16 will adjust the bladders' pressure to set point to produce an ideal fit for subsequent activity, at set pressure levels in the bladders against the residuum's tissue.

A further aspect of the control system 16 is that the fluid should be able to be discharged from all of the bladders rapidly. This is achieved with the fluid bypass return 30. For example, doffing prosthesis at night is ubiquitous among amputees because the residuum tissue and socket must be washed every day and because resting in bed at night without the confinement of the prosthesis is preferred. In order to doff and don the prosthesis easily, the fluid bypass return 30 creates maximum intra-socket volume by draining all of the fluid from the bladders around the pressure relief regulator, which otherwise would have maintained fluid in the bladder to a preset level. After donning in the morning, the fluid bypass return 30 is closed. Then, after the amputee takes 10–20 steps, the set pressure(s) is re-established automatically in each bladder 14 as fluid is pumped from the reservoir 10 to the pumping bladder 12 to the bladder(s) 14 as previously described. If, during the day there is any loss of fluid from the bladders due to perfusion through the bladder walls, the bladders are automatically refilled by the control system 16 to the set pressure(s)of the pressure regulator(s) 26 as soon as the amputee walks.

The present invention serves a number of additional advantageous functions over the existing art such as compensation for neural dysfunction. Vascular dysfunction, usually caused by arteriosclerosis, is the cause of about 75% of TT amputations. Neural dysfunction often accompanies vascular dysfunction; then the TT amputee will have little or no pain response to warn of ischemia. Sores and ulcers are a common outcome. The dynamic fitting system actually will replace the dysfunctional nerves' function by eliminating ischemia (caused by pinching off the capillary blood flow) and so should eliminate tissue necrosis (ulcers) from undetected and excessive socket pressure.

Alternative methods for pumping the fluid include electronic activation, electromechanical activation, and magnetohydrodynamic actuation. All of these methods can be used individually or in combination.

Figure 3C:
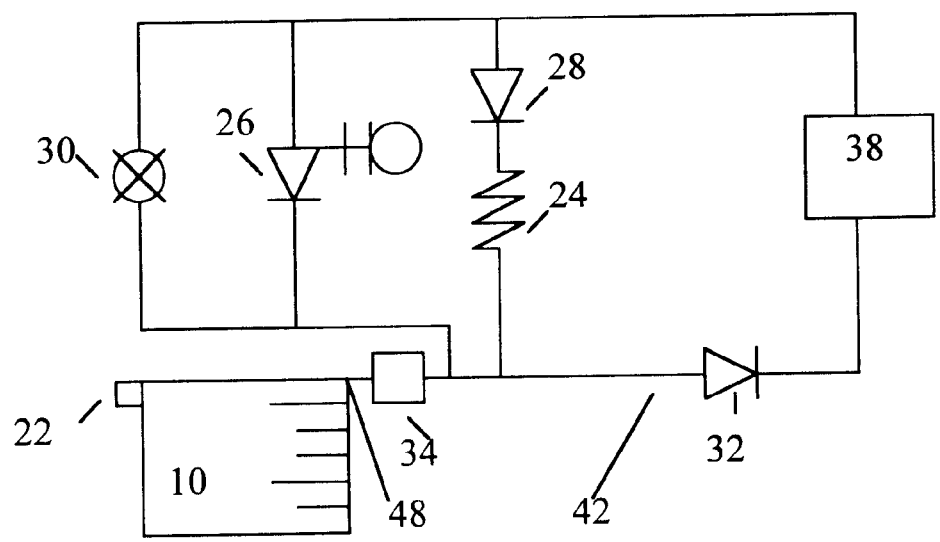
FIG. 3c is a schematic representation of an alternative embodiment control system of this invention for a single bladder system.

An alternative embodiment to a multi-bladder pumping and pressure system is a single bladder system, shown in FIG. 3c, designed to perform the equivalent functions. The single bladder 38 is an integral pumping and pressure bladder. The single bladder will draw fluid from the reservoir to maintain a predetermined pressure within the same bladder while being regulated by pressure regulators and resistors as disclosed in the preferred attachment system. The single bladder will be configured to the amputee's residuum for maximum comfort and securement to the socket.

Mode of Operation

A lower-limb amputee whose suction socket prosthesis is fitted with the preferred system 8 would don their prosthesis by placing their residuum in the socket 18. The fluid bypass return 30, could be open or closed, and there could be fluid in the pressure bladders 14, or the pressure bladders 14 could be empty.

Prior to walking, the fluid bypass return 30, is closed, eliminating this return path for fluid to the reservoir 10. As the amputee walks, pressure in the system fluctuates above and below reservoir pressure. When pressure is below reservoir pressure, fluid is drawn from the reservoir 10 into the pumping bladder 12. When pressure is above reservoir pressure, fluid in forced from the pumping bladder 12 to the pressure bladders 14 through the conduits 42.

Pressure in the pumping bladders 12 and pressure bladders 14 will not exceed the pressure set in the pressure regulator 26. Fluid is continuously returned to the reservoir 10, through the leakage resistor 24, as long as the pressure is above the set pressure of the pressure relief regulator 28.

The prosthesis can be removed at anytime the user desires. If the system is still pressurized and there is not enough volume in the socket 18 for the residuum to be removed, the fluid bypass return 30 can be actuated, thereby returning substantially all of the fluid in the pressure bladders 14 and the pumping bladders 12 to the reservoir 10.

Although the invention has been described with respect to various embodiments, it should be realized this invention is also capable of a wide variety of further and other embodiments within the spirit and scope of the appended claims. Although the system is illustrated with a leg prosthetic, the dynamic variable geometry fitting system is adaptable to other body appliances such as ski boot, boots (including sports boots), shoes, sneakers, prosthetic appliance, orthopedic appliance, brace, or body part wrap, and virtually anything that is designed to be worn on a body part.

What is claimed is:

1. A variable geometry attachment fitting system for use in conjunction with a body appliance to be removably attached to a body part, comprising:

a reservoir of non-leaking material, said reservoir having reservoir filling means for adding fluid to or removing fluid from said reservoir;

at least one pressure bladder made of a substantially pliable fluid-tight material capable of conforming to at least a portion of the appropriate soft tissue areas of the body part, said at least one pressure bladder having a fluid inlet, wherein said at least one pressure bladder is disposed between the body part and the body appliance;

at least one pumping bladder made of a substantially pliable fluid-tight material, said at least one pumping bladder operates as an automatic fluid pump communicating between said reservoir and said at least one pressure bladder for delivering pressurized fluid stored in said reservoir to said at least one pressure bladder, such that the pressure within said at least one pressure bladder may be increased with movement;

a fluid circuit operably interconnected between said reservoir, said at least one pumping bladder, and said at least one pressure bladder, said fluid circuit including pressure control means for regulating and maintaining a predetermined pressure in said at least one pressure bladder; and said pressure control means comprises means for providing controlled leakage of the fluid from within said at least one pressure bladder, such that the pressure within said at least one pressure bladder may be decreased.

2. The system as recited in claim 1, comprises a plurality of pressure bladders.

3. The system as recited in claim 1, wherein said pumping bladder also acts as a pressure bladder.

4. The system as recited in claim 3, wherein said pumping bladder and said at least one pressure bladder constitute a single unit.

5. The system as recited in claim 1, wherein said pressure control means comprises pressure regulation means for allowing excess fluid to return to said reservoir, and said pressure regulation means includes at least one pressure regulator.

6. The system as recited in claim 5, wherein said pressure regulation means further comprises at least one pressure relief regulator.

7. The system as recited in claim 5, wherein said leakage means comprises at least one leakage resistor.

8. The system as recited in claim 7, wherein said at least one leak resistor continuously returns fluid to said reservoir.

9. The system as recited in claim 5, wherein said pressure regulation means further comprises at least one fluid bypass return.

10. The system as recited in claim 5, wherein said pressure control means further comprises at least one flow control valve for preventing fluid from flowing between said at least one pumping bladder and said at least one pressure bladder, and back into said reservoir.

11. The system as recited in claim 5, wherein said pressure control means further comprises at least one filter for preventing particulate debris from entering said at least one pumping bladder and said at least one pressure bladder, and clogging said fluid circuit.

12. The system as recited in claim 5, wherein said at least one pressure relief regulator is set at approximately a tissue ischemic limit of said body part.

13. The system as recited in claim 1, wherein the body part is a residuum.

14. The system as recited in claim 1, wherein the body appliance is a prosthesis.

15. The system as recited in claim 1 wherein the body appliance comprises a means for encompassing said reservoir, said at least one pressure bladder, said at least one pumping bladder and said fluid circuit.

16. The system as recited in claim 15, wherein the body appliance is a prosthesis.

17. The system as recited in claim 15, wherein the body appliance is a ski boot.

18. The system as recited in claim 15, wherein the body appliance is a shoe.

19. The system as recited in claim 15, wherein the body appliance is a boot.

20. The system as recited in claim 15, wherein the body appliance is a sneaker.

21. The system as recited in claim 1, wherein said fluid circuit includes a fluid conduit network.

22. The system as recited in claim 1, wherein said reservoir filling means is a septum.

23. The system as recited in claim 1, wherein said reservoir comprises a fluid consumption indicator.

24. The system as recited in claim 1, wherein said at least one pressure bladder and said at least one pumping bladder are made of biocompatible medical grade urethane material.

25. The system as recited in claim 1, wherein said at least one pressure bladder and said at least one pumping bladder are made of non-biocompatible medical grade urethane material and the body part is not in direct contact with said at least one pressure bladder and at least one pumping bladder.

26. A fluid, volume-compensating attachment fitting system comprising:

engaging means disposed between two opposing objects for applying a sufficient force to the surfaces of the two opposing objects where a first opposing object is removably retained within a second opposing object;

pressurizing means for automatically increasing pressure within said engaging means, whereby said engaging means expands and fills the volume between the two opposing objects to a predetermined pressure, such that the pressure within said engaging means may be increased with movement;

pressure control means for regulating the predetermined pressure within said engaging means; and said pressure control means comprises means for providing controlled leakage of the fluid from within said engaging means, such that the pressure within said engaging means may be decreased.

27. The system as recited in claim 26, wherein said engaging means comprises at least one engaging bladder.

28. The system as recited in claim 26, wherein said pressurizing means comprises at least one pumping bladder.

29. The system as recited in claim 26, wherein said pressurizing means also acts as an engaging means.

30. The system as recited in claim 26, wherein said pressure means and said engaging means are a single unit.

31. The system as recited in claim 26, wherein said pressure control means comprises pressure regulation means for allowing excess fluid to return to said reservoir, and said pressure regulation means includes at least one pressure regulator, at least one pressure relief regulator, at least one leakage resistor, at least one fluid bypass return, and at least one flow control valve.

32. The system as recited in claim 31, wherein said fluid circuit includes a fluid conduit network.

33. An automatic force applying retention system, comprising:

a plurality of bladders being disposed between a body part and a body appliance;

means for automatically adjusting said plurality of bladders with a fluid, wherein said plurality of bladders cooperate to define a body part engaging surface, said body part engaging surface of said plurality of bladders being capable of conforming to at least a portion of an outer surface of said body part when said plurality of bladders are inflated and filling a space between the body part and the body appliance; and said means for automatically adjusting said plurality of bladders comprise a pumping bladder for automatically supplying pressurized fluid to a plurality of pressure bladders upon movement of the body part and leakage means for providing controlled leakage of pressurized fluid from said plurality of bladders.

34. The system as recited in claim 33, wherein said means for automatically inflating said plurality of bladders further comprises an independent pressure control means for each of said plurality of bladders.

35. The system as recited in claim 33, wherein said means for automatically inflating said plurality of bladders further comprises a single pressure control means for said plurality of bladders.

36. The system as recited in claim 33, wherein said means for automatically inflating said plurality of pressure bladders comprises at least one pump and at least one valve for selectively inflating and deflating said plurality of pressure bladders separately and independently to achieve a comfortable and secure fit of the body appliance on the body part.

37. The system as recited in claim 33, wherein said means for automatically inflating is actuated while walking.

38. The system as recited in claim 33, wherein said means for automatically inflating is actuated by manual means, electronic means, electromechanical means, magnetohydrodynamic means or a combination thereof.

39. The system as recited in claim 38, wherein said means for automatically inflating is actuated by a negative pressure in said pumping bladder such that said pressurized fluid is drawn into said pumping bladder during a portion of pumping cycle defined by movement of said body part and by a positive pressure in said pumping bladder such that said pressurized fluid is pumped from said pumping bladder during a different portion of pumping cycle defined by movement of said body part.

40. The system as recited in claim 33, wherein said fluid is substantially incompressible.

41. The system as recited in claim 33, wherein said fluid is incompressible.

42. A lower-limb prosthesis socket system, comprising:
a socket, said socket having a lower-limb prosthesis associated therewith;
a reservoir, said reservoir capable of being filled with a fluid;
at least one pumping bladder, said at least one pumping bladder being positioned near a distal-end of said socket;
a plurality of intrasocket bladders, said at least one pumping bladder being capable of pumping fluid to said plurality of intrasocket bladders during a positive pressure phase and said at least one pumping bladder being capable of drawing fluid from said reservoir during a negative pressure phase such that said plurality of intrasocket bladders create a continuously secure fit for the lower-limb prosthesis socket to a residuum, which is naturally changing volume; and
a plurality of conduits, said plurality of conduits connect said reservoir to said at least one pumping bladder and said plurality of intrasocket bladders, whereby said at least one pumping bladder and said plurality of intrasocket bladders are maintained at a predetermined pressure.

43. The system as recited in claim 42 further comprising an inlet check valve and an outlet check valve, said check valves being disposed between said reservoir and said at least one pumping bladder connected by said conduits, said plurality of check values prevent the fluid from flowing from said plurality of intrasocket bladders back into said at least one pumping bladder, whereby said check valves define pumping action of said at least one pumping bladder.

44. The system as recited in claim 42, further comprising at least one adjustable pressure-relief valve, said at least one adjustable pressure-relief valve being disposed between said reservoir and said at least one pumping bladder connected by said conduits, whereby said at least one adjustable pressure-relief valve can set the pressure in said plurality of intrasocket bladders during stance.

45. The system as recited in claim 42, further comprising at least one leakage resistor being disposed between said plurality of intrasocket bladders and said reservoir, said leakage resistor being disposed between said at least one pumping bladder and said reservoir, whereby said at least one leakage resistor allows fluid to leak from said intrasocket bladders to said reservoir, thereby maintaining a predetermined pressure automatically in said plurality of intrasocket bladders and said pumping bladder below the ischemic limit to relax the pressure against the residuum if stasis is maintained for more than a few minutes.

46. The system as recited in claim 42, further comprising at least one discharge valve being disposed between said bladders and said reservoir, whereby said at least one discharge valve discharges all of the liquid from said plurality of intrasocket bladders and said at least one pumping bladder back into said reservoir to facilitate the removal of said lower-limb prosthesis.

47. The system as recited in claim 42, said reservoir being made of a flexible material, whereby said flexible material will collapse and expand as fluid levels fluctuate.

48. The system as recited in claim 42, wherein said reservoir comprises a reservoir filling means, said reservoir filling means includes an opening to receive a syringe or equivalent for filling and draining said reservoir with fluid.

49. The system as recited in claim 42, wherein said reservoir further comprises a fluid capacity between 100–300 ml.

* * * * *